US00RE40402E

(19) United States
(12) Reissued Patent
Leonhardt et al.

(10) Patent Number: US RE40,402 E
(45) Date of Reissued Patent: Jun. 24, 2008

(54) NON-INVASIVE METHOD FOR OPTIMIZING THE RESPIRATION OF ATELECTATIC LUNGS

(75) Inventors: Steffen Leonhardt, Aachen (DE); Stephan Böhm, Lauenburg (DE)

(73) Assignee: Maquet Critical Care AB, Solna (SE)

(21) Appl. No.: 11/339,819

(22) Filed: Jan. 25, 2006

Related U.S. Patent Documents

Reissue of:
(64) Patent No.: 6,612,995
Issued: Sep. 2, 2003
Appl. No.: 09/917,232
Filed: Jul. 26, 2001

U.S. Applications:
(63) Continuation of application No. PCT/EP00/00685, filed on Jan. 28, 2000.

(30) Foreign Application Priority Data

Jan. 29, 1999 (DE) ..... 199 03 618
Jan. 29, 1999 (DE) ..... 199 03 584

(51) Int. Cl.
*A61B 5/08* (2006.01)
*A61N 16/00* (2006.01)
*A62B 7/00* (2006.01)
*A16K 31/02* (2006.01)

(52) U.S. Cl. ..... 600/532; 600/538; 128/204.23

(58) Field of Classification Search ..... None
See application file for complete search history.

(56) References Cited

U.S. PATENT DOCUMENTS

| | | | | |
|---|---|---|---|---|
| 5,103,814 | A | 4/1992 | Maher | |
| 5,388,575 | A | 2/1995 | Taube | |
| 5,660,170 | A | 8/1997 | Rajan et al. | |
| 5,738,090 | A | 4/1998 | Lachmann et al. | |
| 5,752,509 | A | 5/1998 | Lachmann et al. | |
| 5,937,854 | A | 8/1999 | Stenzler | 128/204.23 |
| 6,116,241 | A | 9/2000 | Huygen et al. | 128/204.23 |

FOREIGN PATENT DOCUMENTS

EP 0 728 493 A1 8/1996

*Primary Examiner*—Robert I. Nasser, Jr.
(74) *Attorney, Agent, or Firm*—Wolf, Greenfield & Sacks, P.C.

(57) ABSTRACT

The invention relates to a method and an apparatus to identify alveolar opening and collapse of a lung. To automatically generate the settings of ventilator parameters in a simple and gentle way, the hemoglobin oxygen saturation and/or the endtidal $CO_2$ concentration and/or the $CO_2$ output are-measured and processing to detect alveolar opening and closing. From the knowledge of the corresponding airway pressures, a central processing unit may generate the settings of ventilation parameters such that gas exchange is maximal while the mechanical stress of the lung tissue is minimal.

17 Claims, 17 Drawing Sheets

NON-INVASIVE METHOD FOR OPTIMIZING THE RESPIRATION OF ATELECTATIC LUNGS

Matter enclosed in heavy brackets [ ] appears in the original patent but forms no part of this reissue specification; matter printed in italics indicates the additions made by reissue.

This application is a Continuation of prior application No. PCT/EP00/00685, filed on Jan. 28, 2000.

The present invention relates to a method and an apparatus to determine the alveolar opening and/or closing of a lung.

Such a method and such an apparatus are especially useful to optimally set the control variables of an artificial ventilator as both the alveolar opening and the alveolar closing are important parameters of an atelectatic (=partially collapsed) lung.

In German intensive care units (ICUs), approximately 8.000–10.000 are artificially ventilated each day. The ventilator control variables, such as airway pressure ($P_{aw}$) and respiratory rate (RR), are usually chosen based on known standard procedures, but often left constant afterwards and not adapted to the changing needs of a specific patient.

Today, the success of artificial ventilation is evaluated by using arterial blood gas analysis during which the partial pressures of oxygen ($paO_2$) and carbon dioxide ($paCO_2$) are determined. However, quite often these values are measured only 1–4 times a day. Since a human performs about 20.000 breath strokes per day, it becomes obvious that such a low "sampling rate" may not be sufficient to evaluate the status in critical and unstable patients.

Patients with an acute respiratory distress syndrome (ARDS) usually belong to this group of critical patients. Despite all sucesses in intensive care medicine, ARDS still is a pathological state with a mortality of 50%. The basic patho-physiological mechanism is the lack of "surfactant", a substance which reduces suface tension resulting in a collapse of major lung fractions and a dramatically reduced gas exchange area.

To prevent undesirable sequelae and consecutive multiorgan failure, one important goal of protective ventilator therapy should be a gentle and early "reopening" of the lung. Choosing the airway pressures properly has an important impact on this.

Through the identification of the alveolar opening and especially of the alveolar closing pressures, a distressed lung may be kept open by proper choice of the airway pressure. However, the manual determination of opening and closing pressures is arduous and time consuming. To use the present invention in clinical practice, an automatic, computerized strategy is strongly recommended.

Prior to citing known methods to identify a lung collapse, a basic introduction to artificial ventilation shall be given:

The major function of the lung is the gas exchange, i.e. providing sufficient $O_2$ to the circulation and eliminating $CO_2$ from the body. If a human is not capable to perform this gas exchange himself anymore, he must be ventilated artificially.

Figure 1:
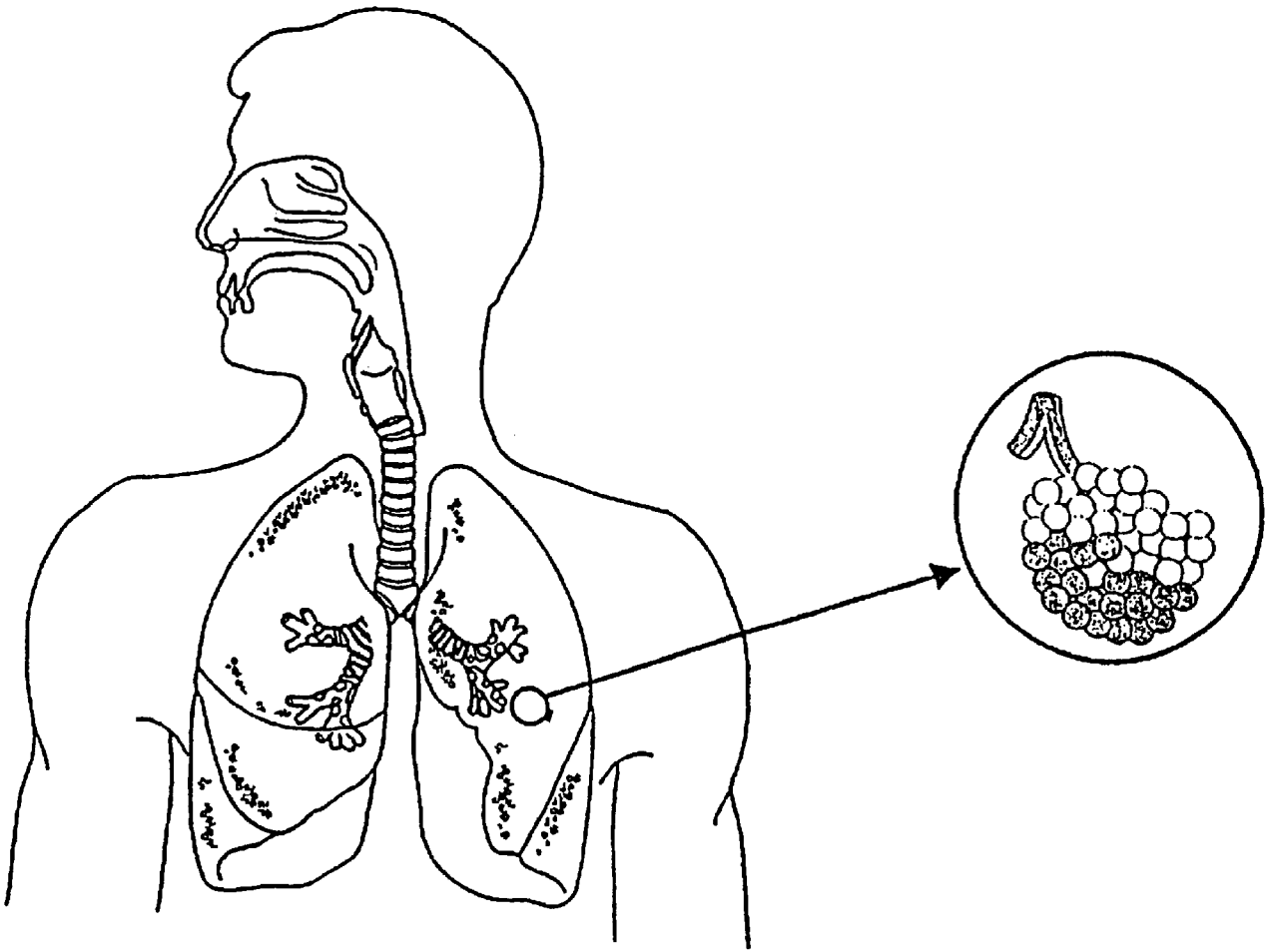

FIG. 1 shows the human bronchial tree and an enlargement of some human alveoles. As in spontaneous ventilation, during artificial ventilation fresh air must be transported via the conducting parts of the brochial tree into the respiratory zone of the lung. The gas exchange actually happens in the so called "alveoli", grape-shaped structures with an average diameter of about 70 μm which are located in the terminal part of the bronchial tree.

During spontaneous ventilation, contraction of the diaphragm produces a subathmospheric pressure within the lung which causes air to be sucked into the lung. By contrst, in most modern forms of artificial ventilation a positive airway pressure is applied to the patient which presses air into the lung ("excess pressure ventilation").

There are two major forms of ventilatory support: assisted (=augmented) and mandatory (=controlled) artificial ventilation.

In augmented artificial ventilation, the activity of the patient is monitored, either by detecting inspiratory flows sufficient to trigger an artificial breath stroke or by allowing the patient to breathe on top of a basic mandatory ventilatory support. These ventilation modes are especially used during weaning from the ventilator. By contrast, controlled mechanical ventilation (i.e. artificial ventilation without spontaneous breathing activity) is usually applied to more severly ill patients in which complete control of the breathing is desirable or necessary.

There are two major forms of controlled mechanical ventilation, namely pressure- and volume-controlled ventilation.

Figure 2:
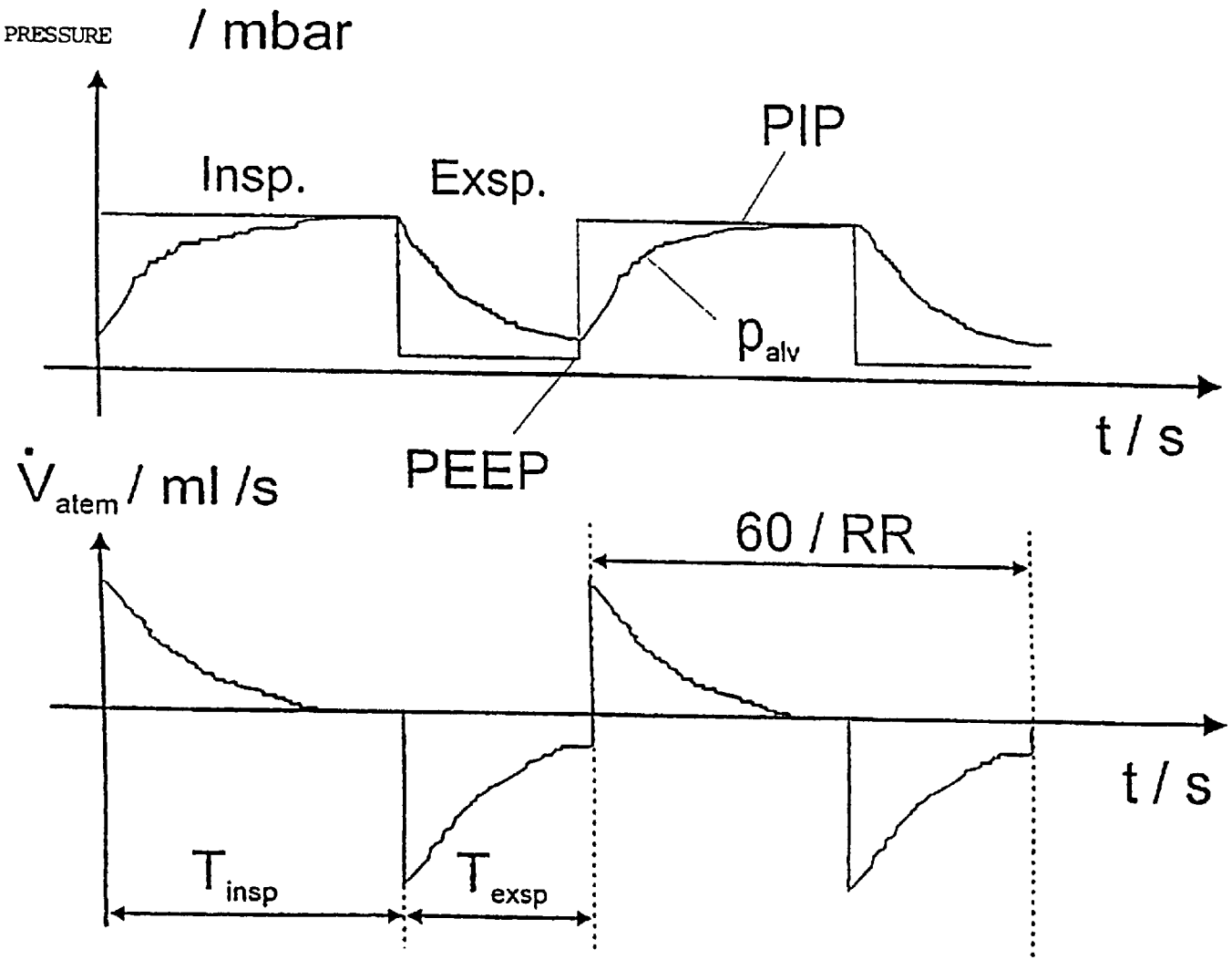

During pressure-controlled ventilation, the airway pressure is kept at desired levels during inspiration as well as during expiration. The corresponding pressure levels may be named, "peak inspiratory pressure" (PIP) and "positive end-expiratory pressure" (PEEP). Note that the alveolar pressure $P_{alv}$ actually varies in between these two pressure levels. FIG. 2 illustrates the time course of airway and alveolar pressure during pressure controlled ventilation.

On the ventilator, several control variables must be adjusted according to the patient needs including the respiratory rate (RR) and the inspiration to expiration ratio (I/E). The following eqn. describe the relationships $$RR = \frac{1}{T_{insp} + T_{exsp}} \cdot \frac{60}{min} \tag{1}$$

and $$I/E = \frac{T_{insp}}{T_{exsp}} \tag{2}$$

with $T_{insp}$ the inspiration and $T_{exp}$ the expiration time. The inspired and exhaled volume during quiet breathing is named tidal volume ($V_T$). Assuming a stationary operation and no leakage in the breathing system, $V_T$ is given by $$V_T = \int_0^{T_{insp}} \dot{V}_{atem}\, dt = \int_{T_{insp}}^{T_{exsp}} \dot{V}_{atem}\, dt \tag{3}$$

Figure 3:
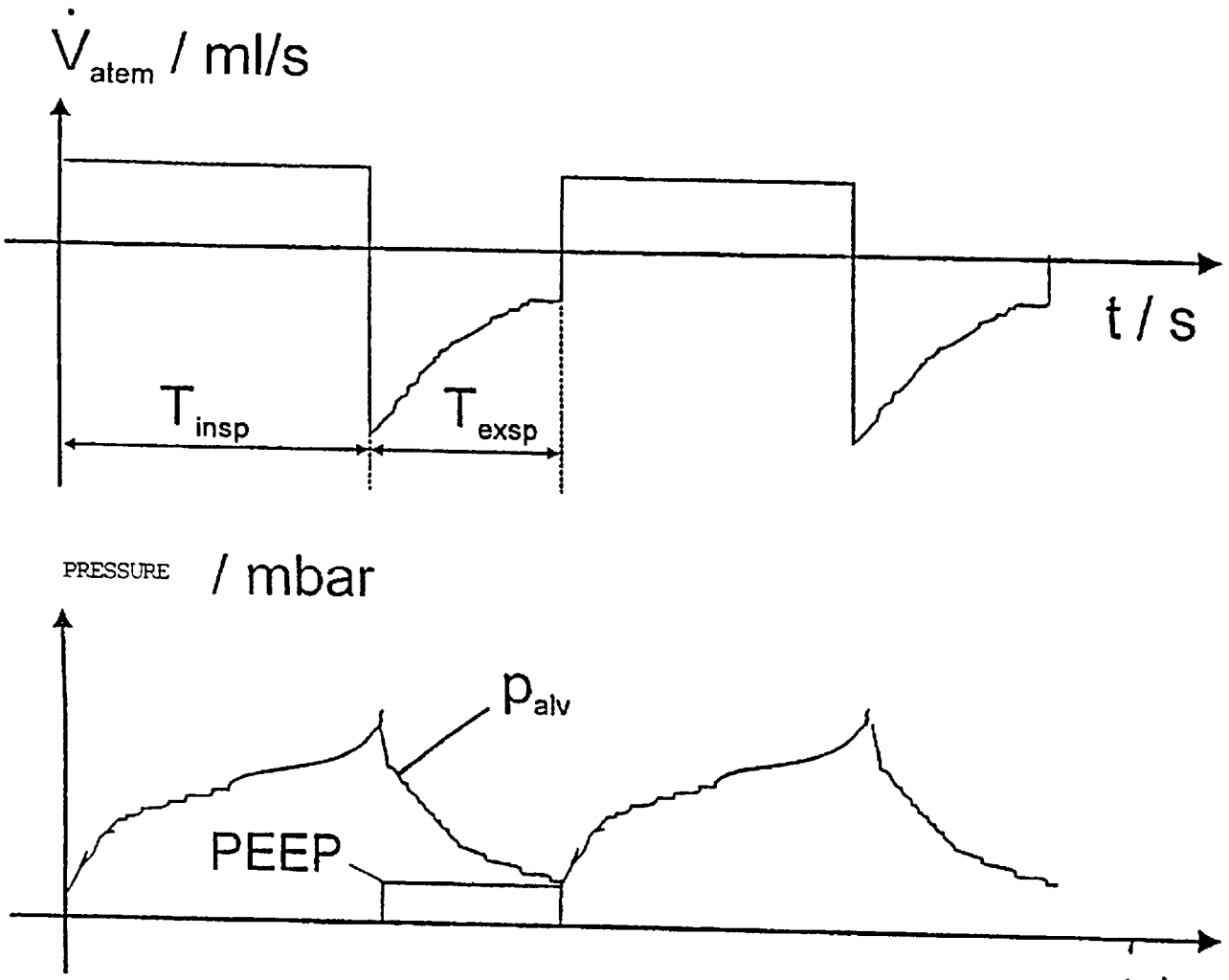

During volume-controlled ventilation, a konstant air flow is applied during inspiration while expiration occurs passively against a given PEEP. FIG. 3 illustrates the time course of airway pressure, alveolar pressure and air flow during volume-controlled ventilation.

Note that volume-controlled ventilation guarantees delivery of a certain tidal volume while pressure-controlled ventilation does not. For this reason, some clinicians still prefer this form of mandatory ventilation. However, depending on the actual lung condition there are major disadvantages. In patients with a stiff lung, for example, $P_{alv}$ may reach undesirable limits and cause barotrauma. Furthermore, due to lung inhomogenities, local lung air flows may arise (so called "Pendelluft").

From Leonhardt, S., Böhm, S. and Lachmann, B. "Optimierung der Beatmung beim akuten Lungenversagen durch Identifikation physiologischer Kenngroessen", Automatisierungstechnik (at), Vol. 46, No. 11, pp 532–539, 1998 as well as from U.S. Pat. Nos. 5,660,170, 5,738,090 and 5,752,509, it is known that the airway pressures required to open or close a specific lung can generally be identified from measurements of the arterial oxygen partial pressure ($paO_2$). After the identification procedure, the authors suggest to ventilate above the closing pressure.

It is known that both the identification and the later selection of ventilator parameters for long-term ventilation can be accomplished automatically by using a computer. A major disadvantage of this known method is that the measurement of this physiological parameter requires expensive and very sensible catheter systems and introduce possible damage to the patient (infections, bleeding, etc.).

Object of the present invention is to automatically provide a setting of ventilator parameters in critical patients.

This object is solved by a method according to the claims 1, 5 and 6 as well as an apparatus according to the claims 9, 11 and 12. By using the new feedback signals as claimed in this invention, in claim 13 an apparatus is presented aiming at automatic protective artificial ventilation of human lungs.

The invention is based on the cognition that the hemoglobin oxygen saturation ($SO_2$), the endtidal $CO_2$ concentration ($etCO_2$) and the $CO_2$ output (the elimination of $CO_2$ volume from the body per unit time) can easily be obtained noninvasively and may be used, either solely or combined as parameters to identify the alveolar opening and closing pressure levels of the lung. An invasive arterial line is not necessary anymore. All three parameters may be measured outside the body and may well be used as feedback signals for automatic artificial ventilation.

Similar to using the arterial oxygen partial pressure ($PaO_2$) as a parameter to identify alveolar opening or closing pressures, $SO_2$ may be used for this task as well. For example, $SO_2$ may be set to e.g. 80% by adjusting the ventilator in a proper way (e.g. adjust the inspiratory oxygen fraction $fiO_2$). An alveolar opening due to a subsequent increase of ventilation pressure may then be detected by a large increase in $SO_2$. Similiarly, an alveolar collapse due to a reduction of ventilation pressure may indeed be detected by a decrease in $SO_2$.

However, using $SO_2$ directly has the disadvantage that the saturation may temporaily reach rather low values which could cause life threatening situations.

Thus, a related object of this invention is to provide a method in which $SO_2$ is feedback controlled to stay around given setpoints by properly adjusting the inspiratory oxygen fraction $fiO_2$ at the ventilator. In fact, if starting from a low level, the airway pressure is increased continuosly, the $fiO_2$ required to keep $SO_2$ constant will decrease while this $fiO_2$ will increase with a reduction of airway pressure.

For an automatic detection of alveolar opening during a continuous increase of airway pressure, one possibilities is to look for the negative maximum of the gradient of $fiO_2$ set by the controller. Similarily, an alveolar closing may be identified by detecting the positive maximum of the gradient of $fiO_2$ set by the controller during a continuous decrease in airway pressure.

Another related object of this invention is to provide a method in which the endtidal $CO_2$ concentration in the exhaled air flow is measured which can be used to detect alveolar opening or closing of the lung.

In addition or instead, the $CO_2$ output from the body may also be measured and used for the same task. Note that the $CO_2$ output ([ml $CO_2$/min]) may be obtained by continuously measuring the $CO_2$ concentration in the expired air as well as the air flow and the respiratory rate.

When the airway pressure is changed during ventilation, the endtidal $CO_2$ concentration and the $CO_2$ output behave similar. Thus, if the airway pressure is increased starting from a low value, the endtidal $CO_2$ concentration and the $CO_2$ output also increase. If the airway pressure is decreased afterwards, the endtidal $CO_2$ concentration and the $CO_2$ output decrease as well.

Within an automatic signal monitoring device, a criterion for alveolar opening can be to e.g. look for a maximal change in the positive gradient of either the endtidal $CO_2$ concentration or the $CO_2$ output when simulataneously increasing the airway pressure continuously starting from a low value. In other words, during a continuous pressure rise alveolar opening occurs when the second time derivative of $etCO_2$ and/or of $CO_2$ output has a maximum while the first derivative is positive.

Similarily, a criterion for alveolar collapse can be e.g. a maximal change in the negative gradient of either the endtidal $CO_2$ concentration or the $CO_2$ output during a continuous decrease in airway pressure. In other words, alveolar closing occurs during a continuous decrease in airway pressure if the second time derivative of $etCO_2$ and/or of $CO_2$ output has a minimum while the first derivative is negative.

In a preferred embodiment of this invention, the methods for identification of alveolar opening or collapse pressures as claimed in this invention may be used to build a device for protective artificial ventilation in which a central processing unit (CPU) uses the identified opening and closing pressures to automatically set at least one ventilation parameter of an artificial ventilator such that a maximal gas exchange can be achieved while simultaneously minimizing mechanical stress on lung tissue.

Further details and advantages will be discussed with reference to the preferred embodiments given in the following figures.

Figure 4:
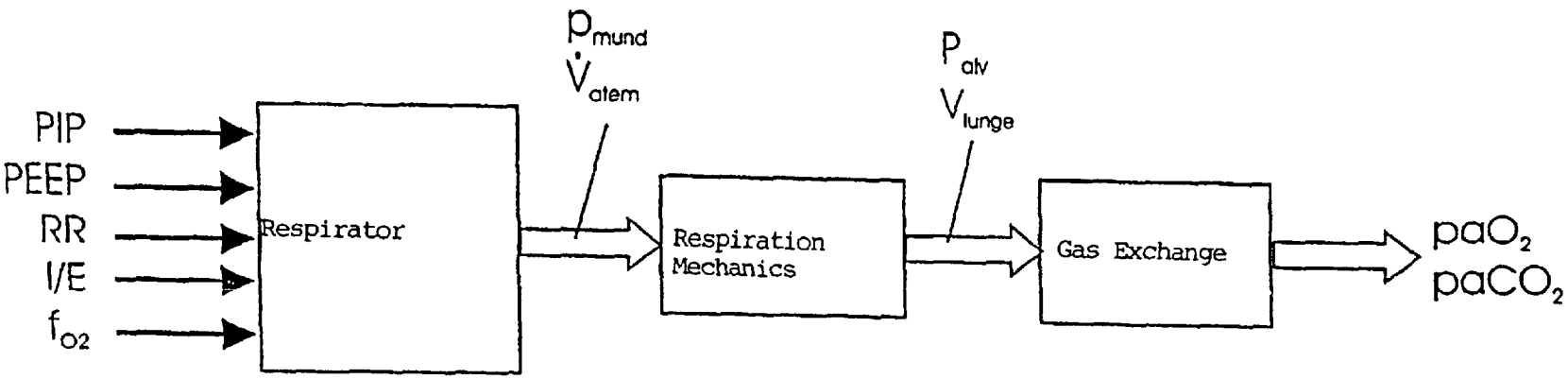
Figure 5:
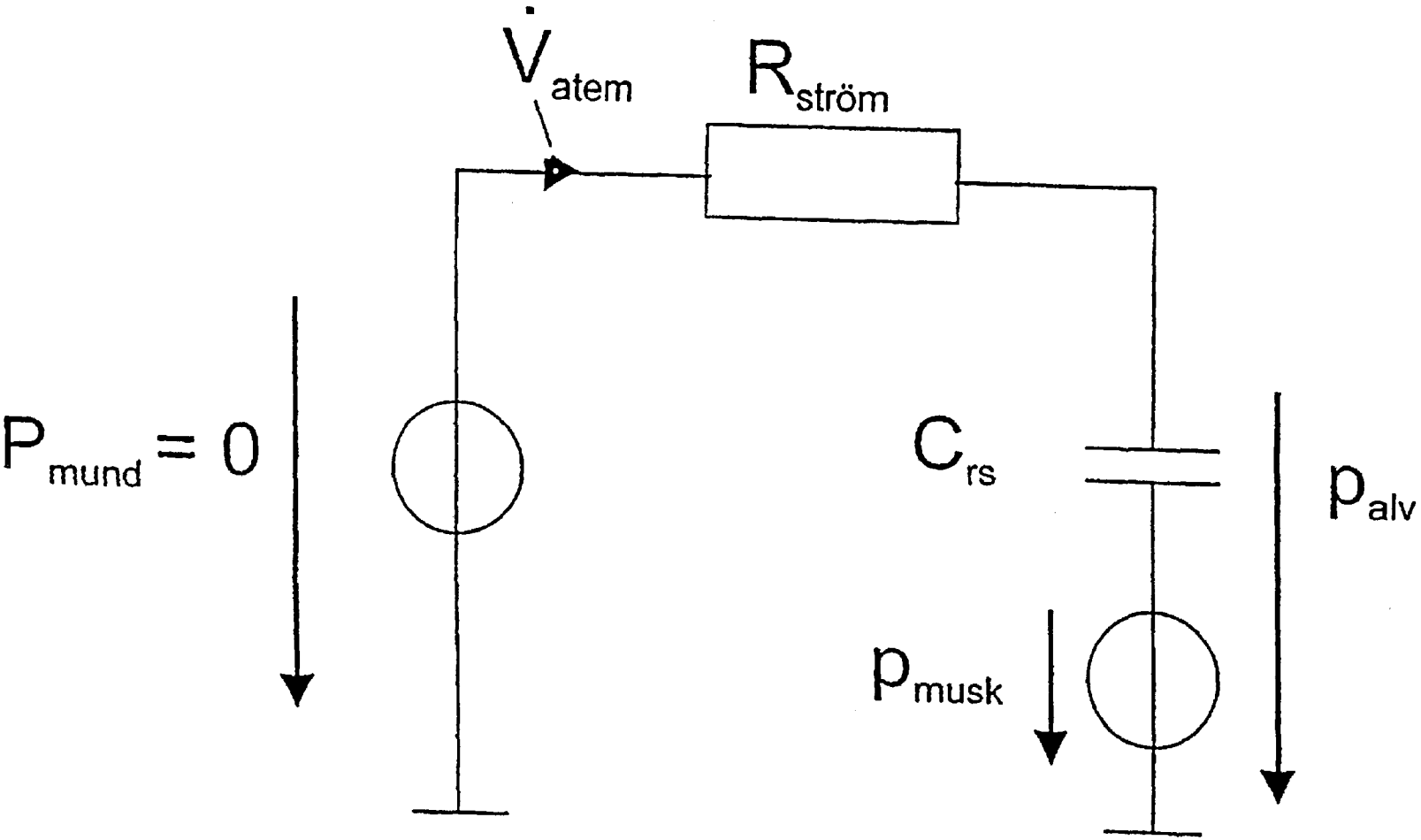
Figure 6:
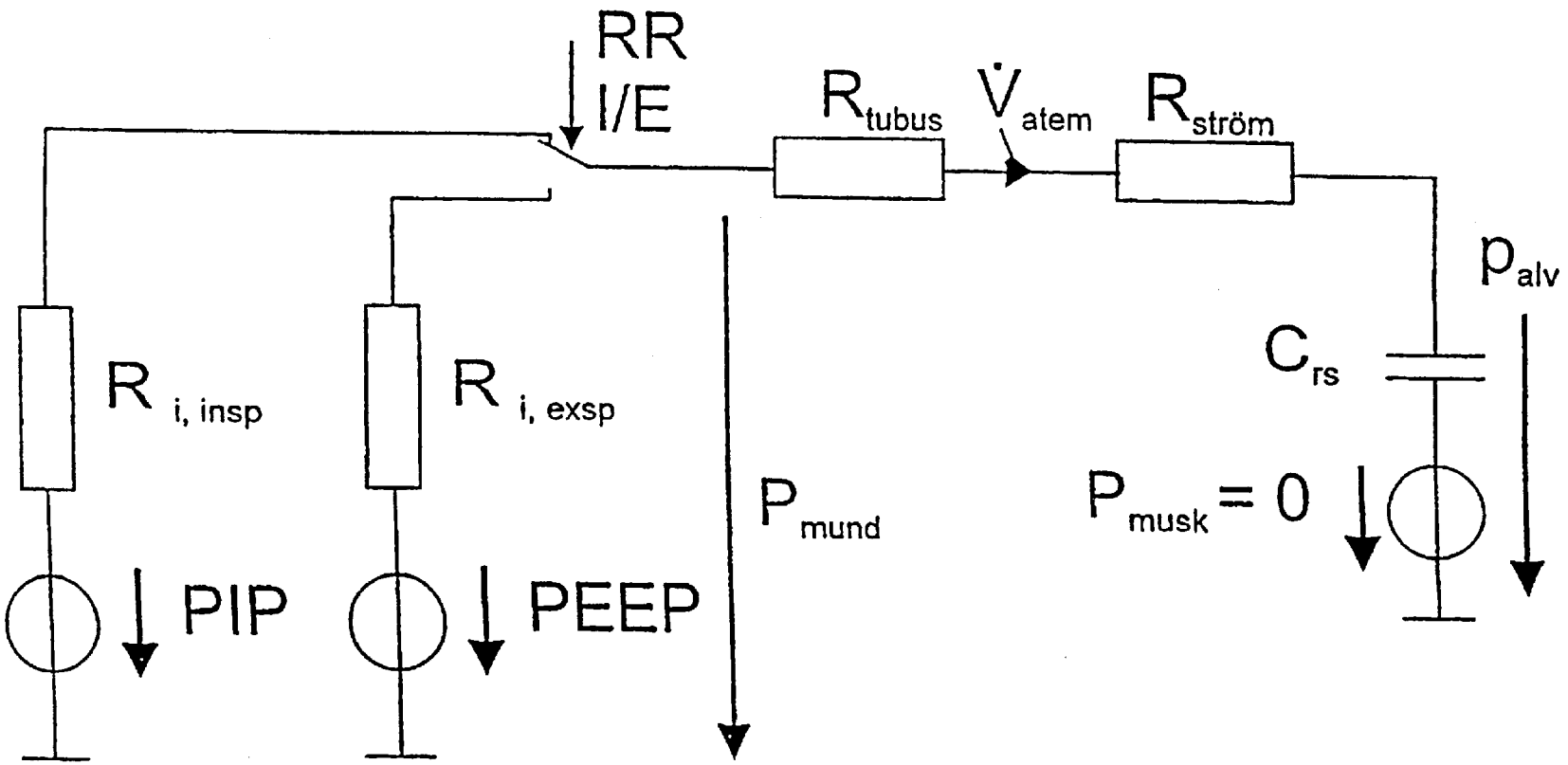
Figure 7:
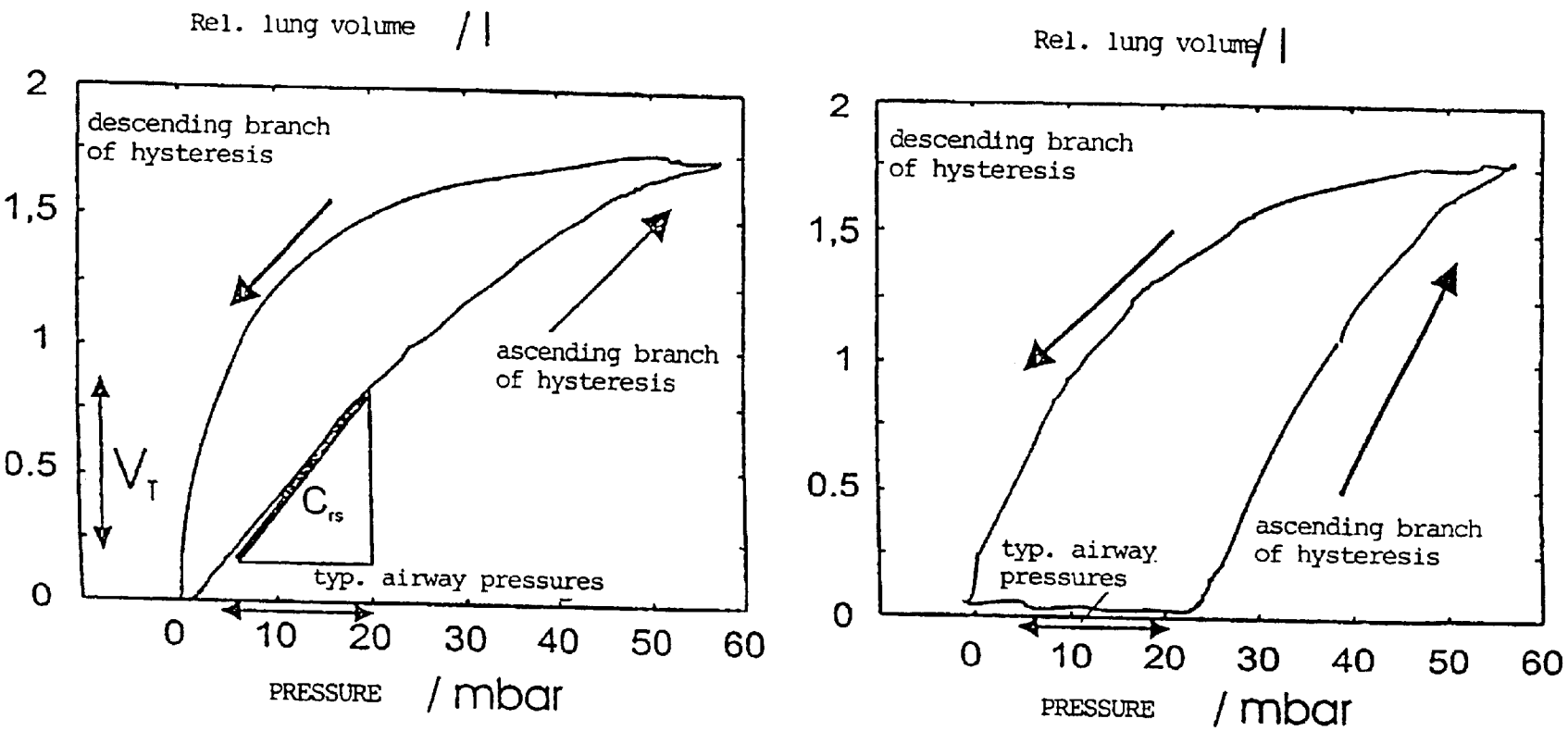
Figure 8:
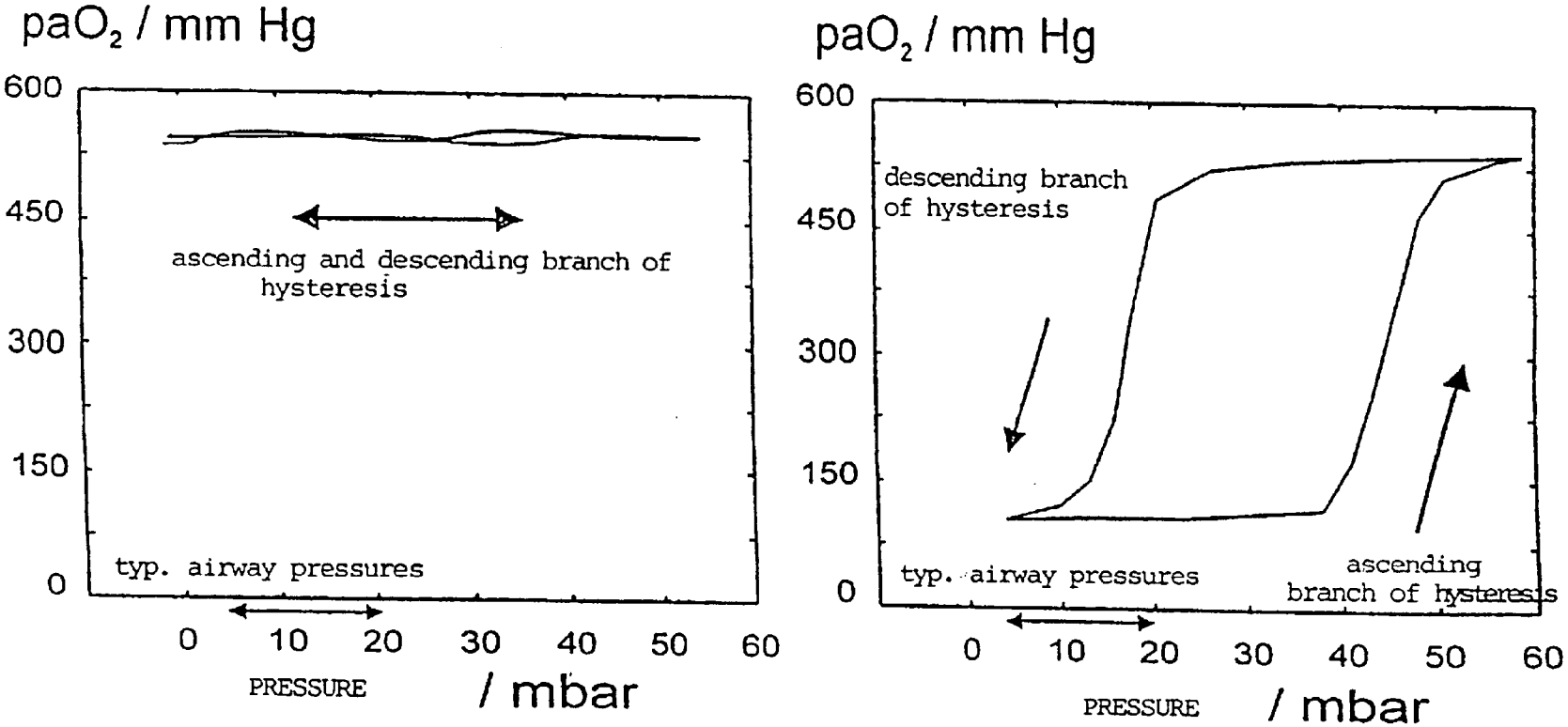
Figure 9:
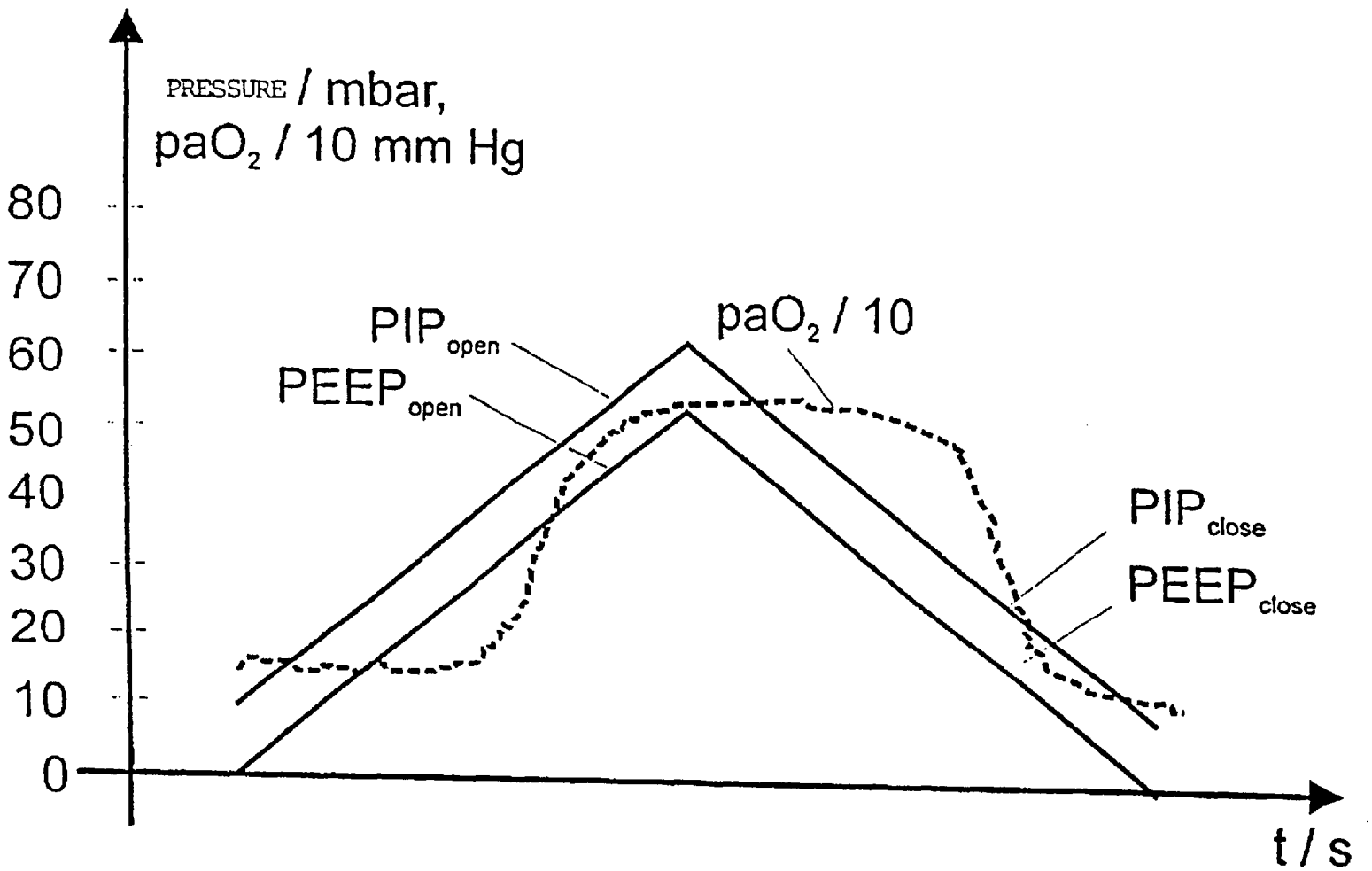
Figure 10:
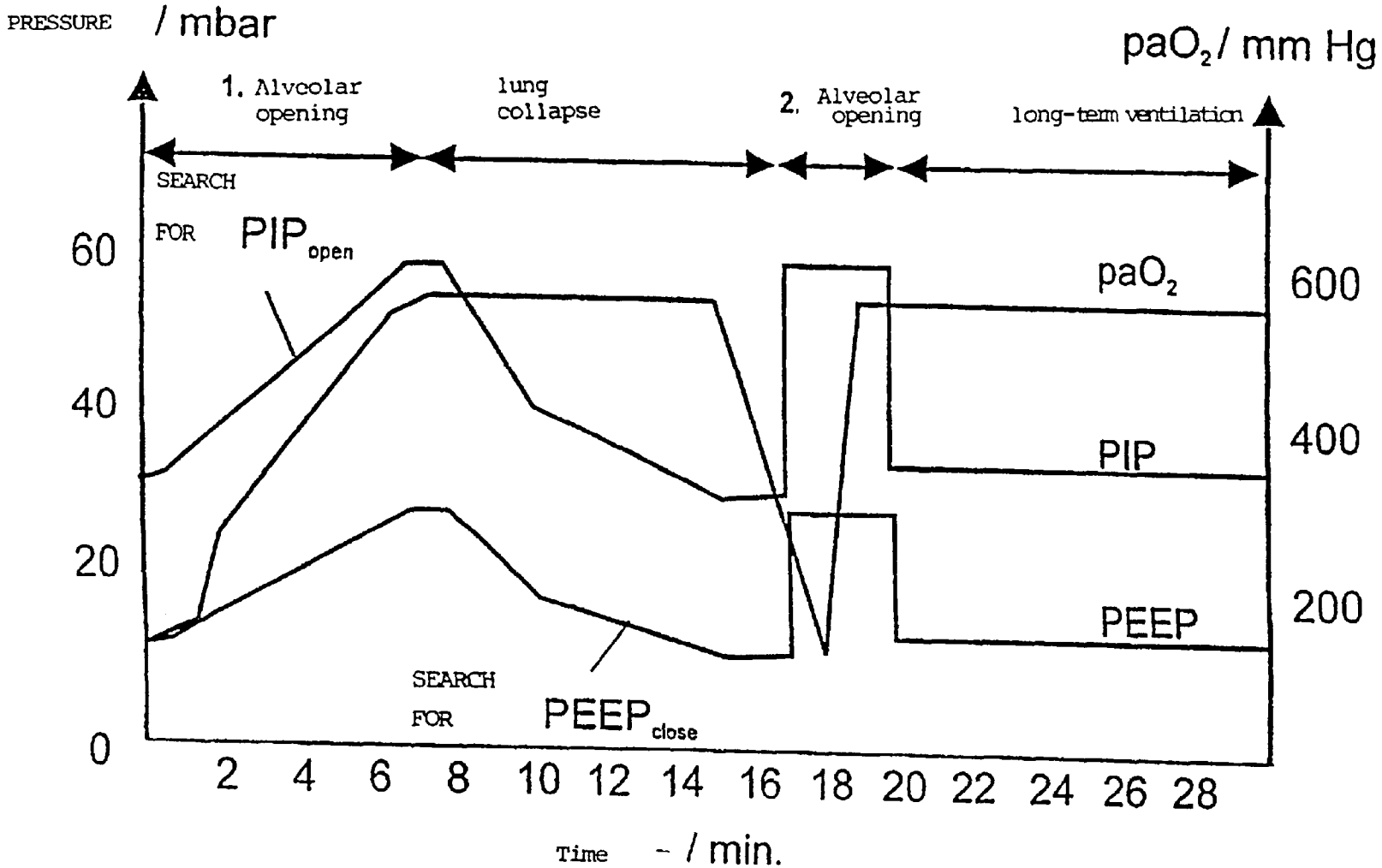
Figure 11:
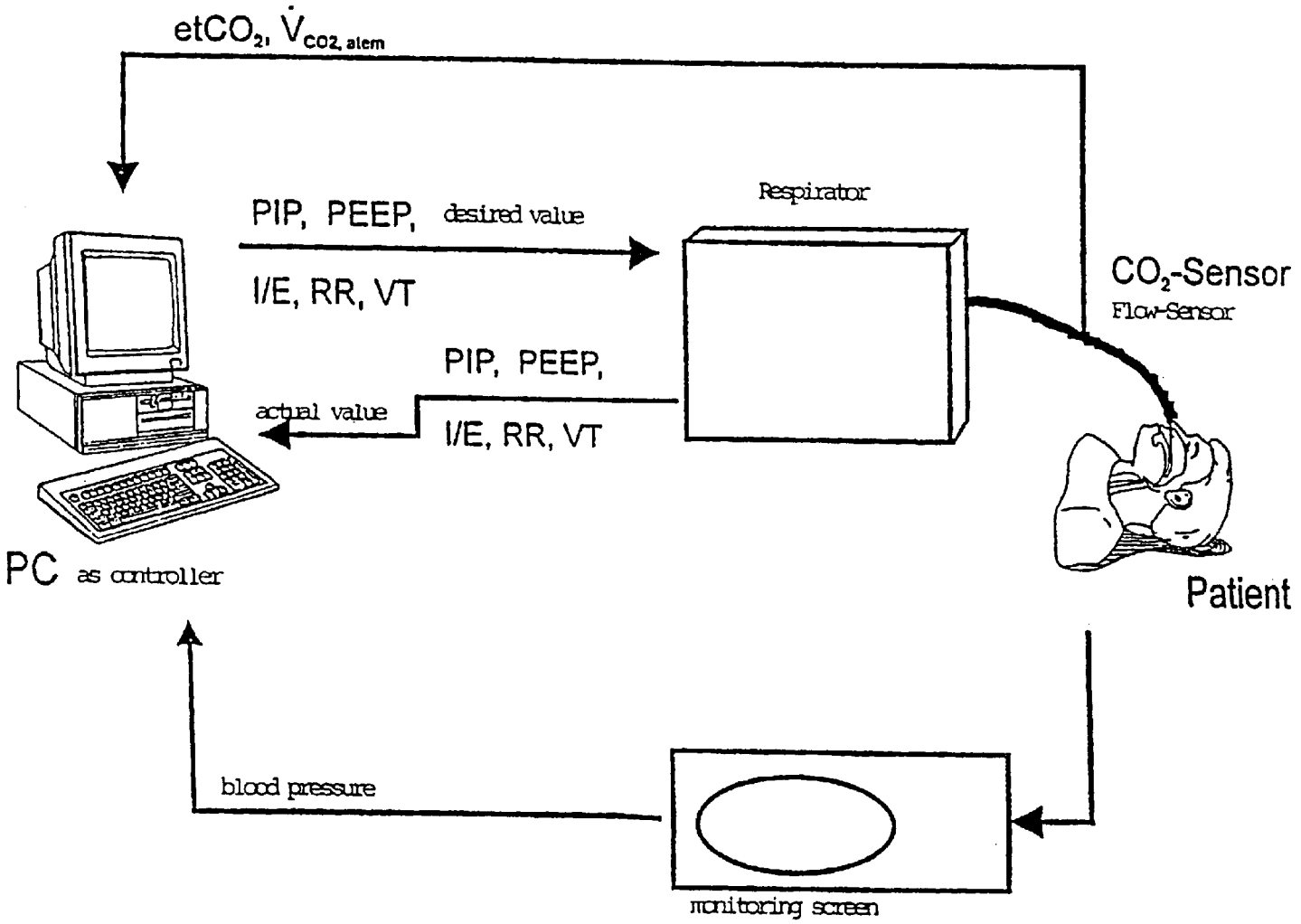
Figure 12:
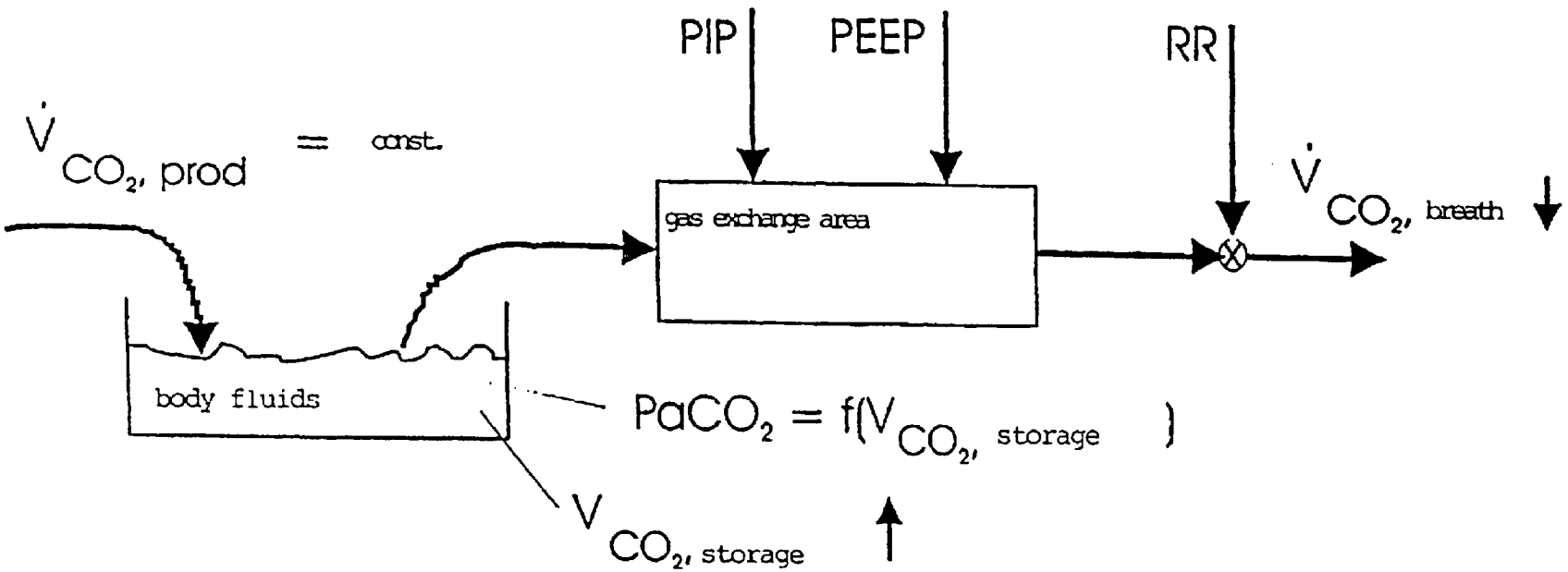
Figure 13:
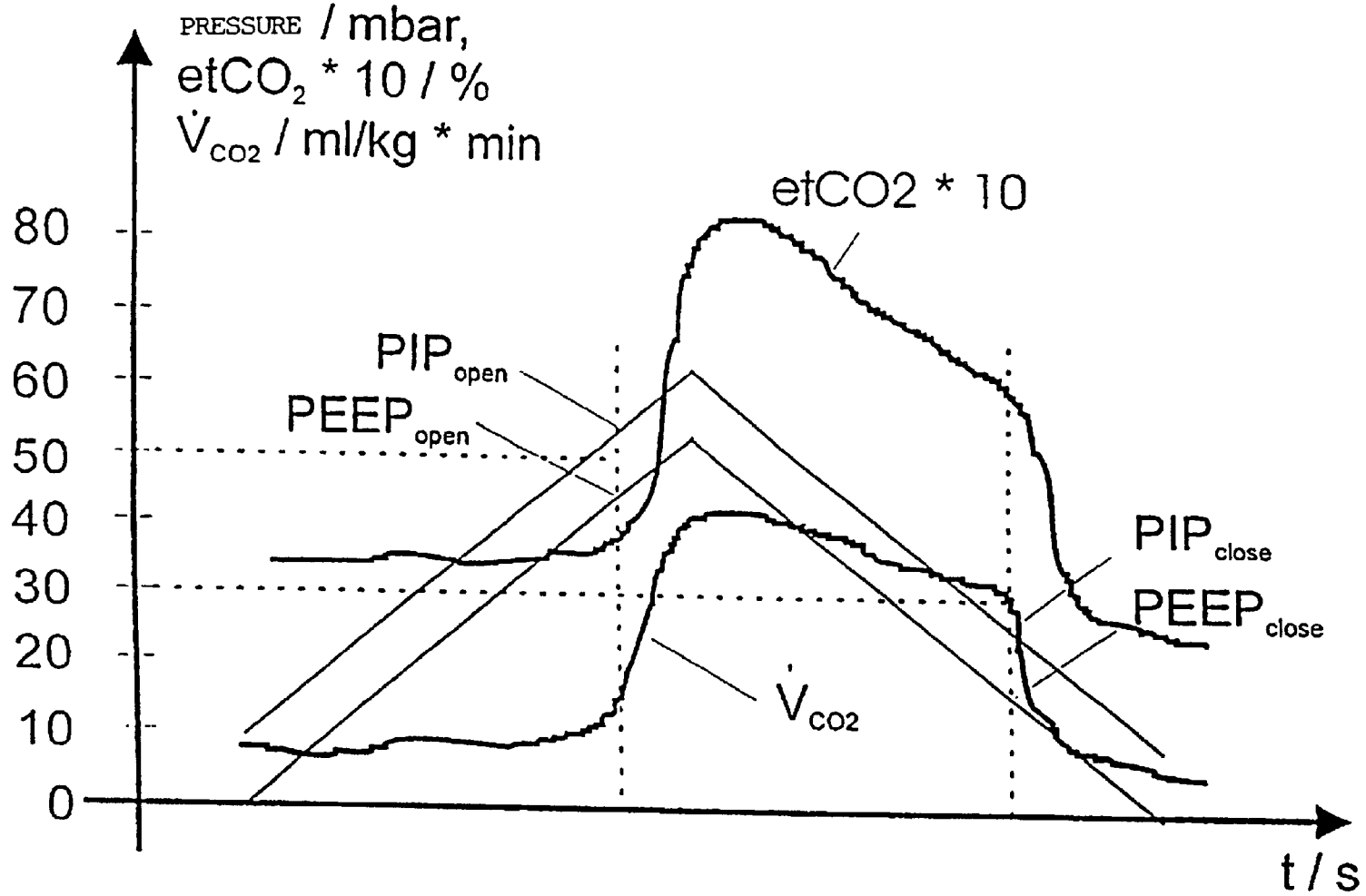
Figure 14:
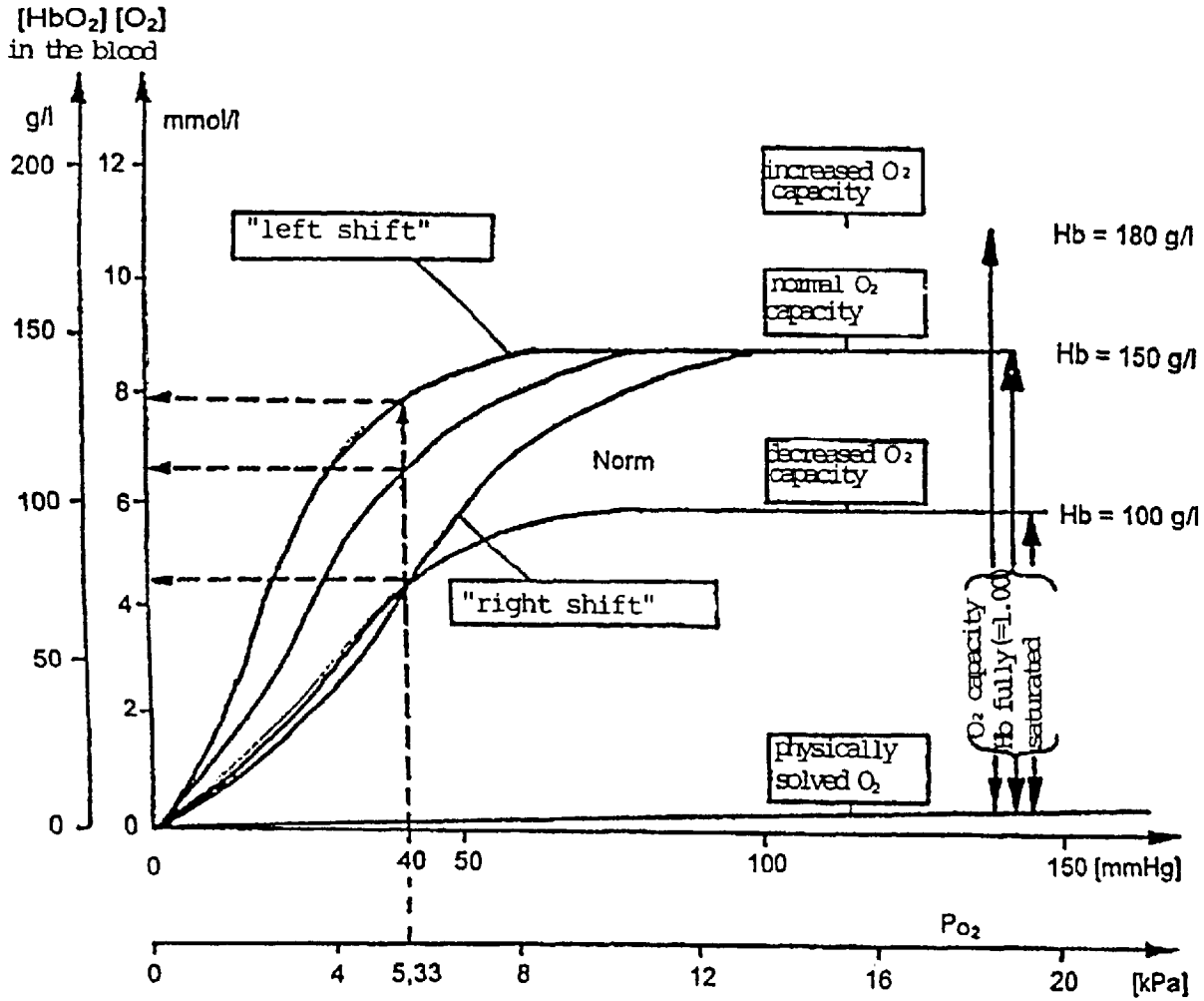
Figure 15:
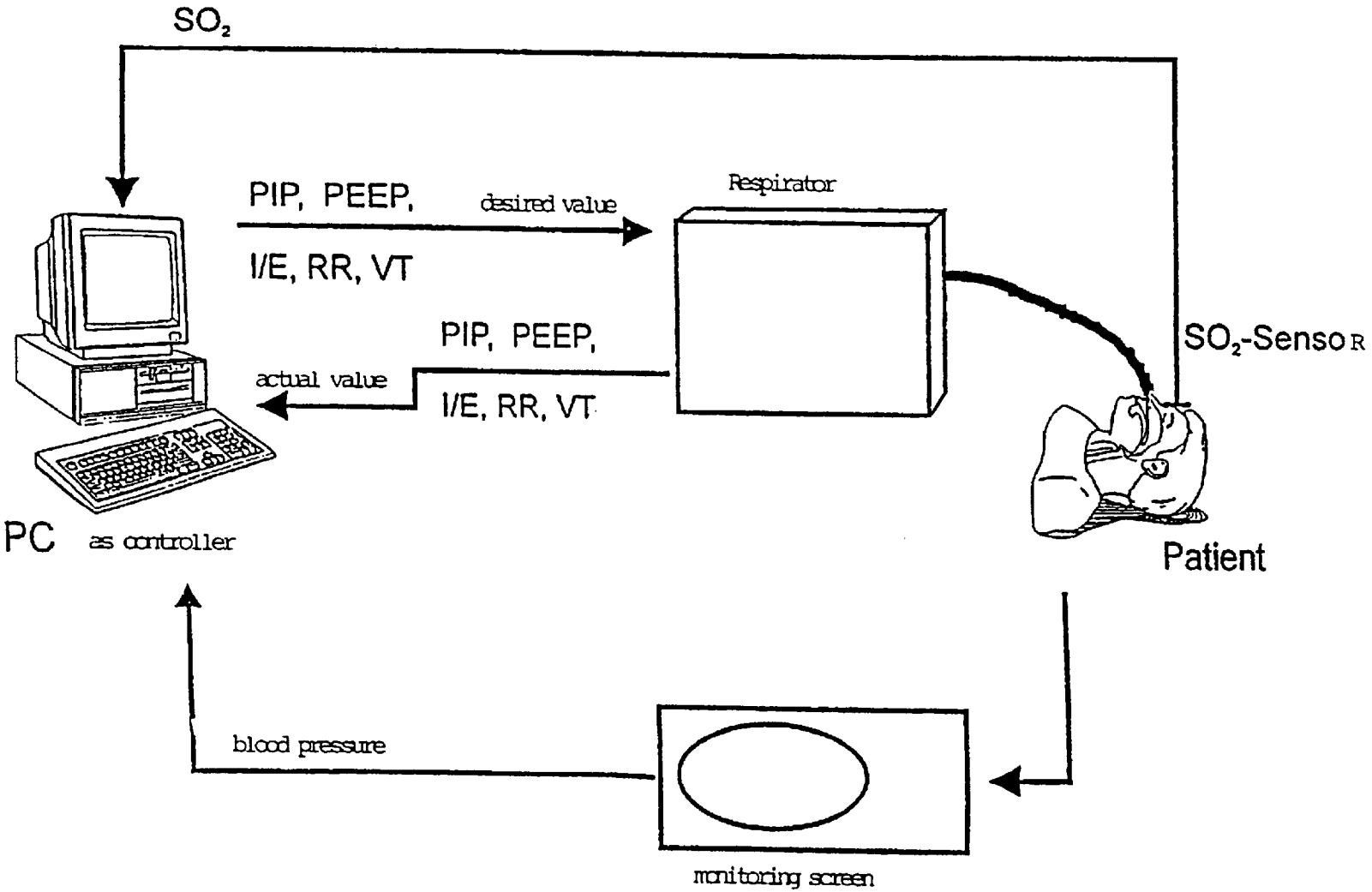
Figure 16:
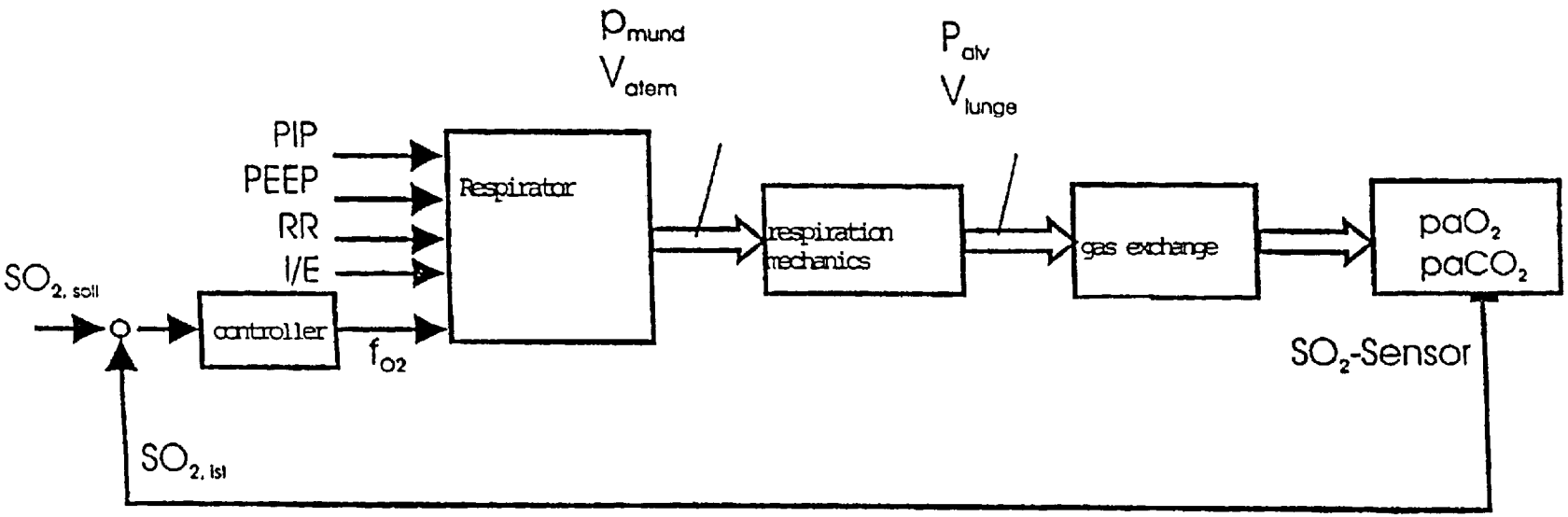
Figure 17:
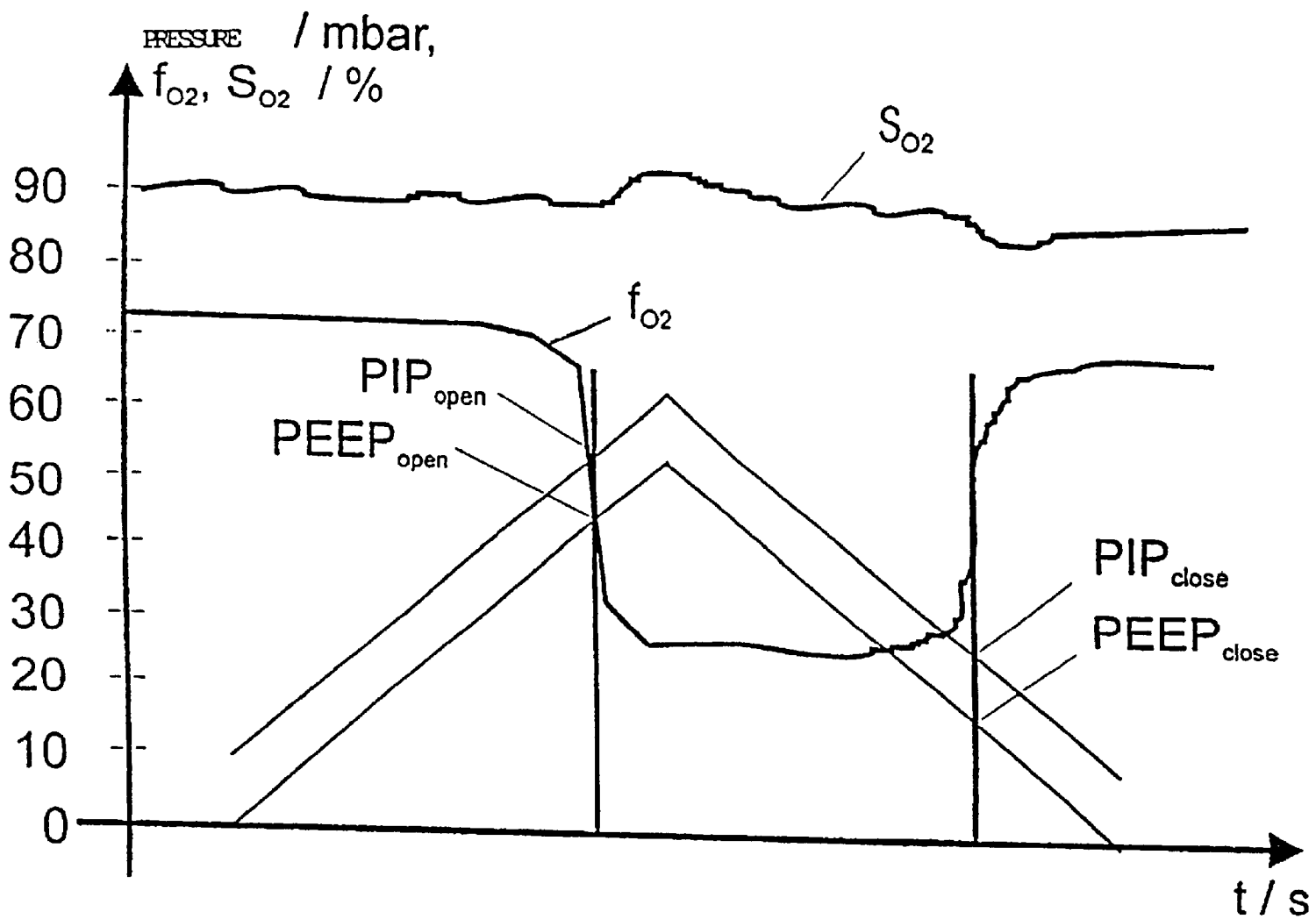

FIG. 1 shows the human bronchial tree and some alveoles in the magnified section, FIG. 2 shows the time courses of airway pressure, alveolar pressure and air flow during pressure controlled ventilation, FIG. 3 shows the time courses of airway pressure, alveolar pressure and air flow during volume controlled ventilation, FIG. 4 shows a block diagram including several signal flows to model artificial ventilation, FIG. 5 shows a electrical analog of lung mechanics during spontaneous breathing, FIG. 6 shows a electrical analog of lung mechanics during pressure controlled ventilation, FIG. 7 shows pV loops of a healthy (left) and of an ailing (right) lung, FIG. 8 shows the $paO_2$ as a function of airway pressure in a healthy (left) and an ailing (right) lung, FIG. 9 shows airway pressure ramps for identification of the large-signal $paO_2$ characteristic of an ailing lung, FIG. 10 shows the application of the method given in FIG. 9 for an protective long-term ventilation, FIG. 11 shows a first preferred embodiment of this invention to achieve an automatic artificial ventilation based on $etCO_2$ and/or $CO_2$ output, FIG. 12 shows a scheme how to obtain $CO_2$ output, FIG. 13 shows airway pressure ramps for identification of the large-signal characteristic of an ailing lung based on $etCO_2$ and/or $CO_2$ output, FIG. 14 shows the correlation between arterial oxygen partial pressure $paO_2$, physically solved $O_2$ and hemoglobin oxygen saturation ($SO_2$), FIG. 15 shows another preferred embodiment of this invention to achieve an automatic artificial ventilation based on $SO_2$, FIG. 16 shows a cascaded feedback control loop in which the inspiratory oxygen fraction ($fiO_2$) is automatically set in order to control the hemoglobin oxygen saturation ($SO_2$) at a given value, FIG. 17 shows airway pressure ramps for identification of the large-signal characteristic of an ailing lung based on the inspiratory oxygen fraction, with reference to FIG. 16.

Note that FIGS. 1 to 3 have already been introduced when describing the prior art.

FIG. 4 shows a block diagram including several signal flows to model artificial ventilation. Such a modeling aims at the identification of the lung by applying the methods claimed in this invention which can be used to automatically tune artificial ventilation such that a maximal gas exchange is obtained while the mechanical stress of the lung is minimized.

Note that for a better understanding of a system and for tuning of control systems, it is generally advisible to obtain a process model first. In the case of artificial ventilation, the model should contain the blocks "ventilator", "lung mechanics" and "gas exchange".

FIG. 4 shows a block diagram including several signal flows to model artificial ventilation. The inputs (ventilator settings) are the peak inspiratory pressure (PIP), the positive endexpiratory pressure (PEEP), the respiratory rate (RR), the inspiration to expiration rate (I/E) and the inspiratory oxygen fraction $fiO_2$ (20 . . . 100%). The outputs of this whole system are the partial pressures of oxygen and carbon dioxide ($paO_2$ and $paCO_2$, respectively) while the actual lung volume ($V_{lung}$) and the alveolar pressure ($P_{alv}$) are internal states of the system. Unfortunately, these states are very difficult to measure and are thus often poorly known.

Especially the subsystems "lung mechanics" and "gas exchange" are very non-linear. Thus, it is important to analyze the large-scale as well as the small-scale characteristics (see FIG. 5).

When analyzing the small-scale behavior, it must be considered that the bronchial tree actually consists of a branching set of tubes which form the "resistance to air flow" ($R_{air}$). In healthy lungs, the major fraction of this resistance is located in generations 3 to 6 of the bronchial tree.

The second parameter that describes small-scale lung mechanics is the so called "compliance of the respiratory system" ($C_{rs}$) which is mainly determined by the elastic properties of the peripheral lung and thorax tissue.

FIG. 5 shows a electrical analog of lung mechanics during spontaneous breathing. Since the mouth pressure is equal to athmospheric pressure during spontaneous breathing, $P_{mouth}=0$ is a proper assumption in this model. From a circuit analysis, the following differential equation can be obtained:

$$P_{musk}(t) + \frac{1}{C_{rs}} \cdot (V_{lunge}(t) - V_{lunge,0}) + R_{ström} \cdot \dot{V}_{atem}(t) = P_{mund} = 0. \tag{4}$$

with $p_{muse}(t)$ the suction pressure caused by contraction of the diaphragm and $V_{lung,\ 0}$ the lung volume at rest. The dynamics of the lung mechanics may be described by the respiratory time constant $$T_{rs}=R_{steam} \cdot C_{rs} \tag{5}$$

For resistance to air flow and respiratory compliance, the following equations yield:

$$R_{ström} = \frac{P_{mund} - P_{alv}}{\dot{V}_{atem}} \tag{6}$$

and $$C_{rs} = \frac{V_{lunge} - V_{lunge,0}}{P_{alv} - P_{musk}} \tag{7}$$

In healthy adult subjects, typical values for resistance and compliance are $R_{air}$=2 . . . 4 mbar s/l and $C_{rs}$=230 . . . 290 ml/mbar. However, both parameters vary strongly with lung volume and are thus functions of the operating point.

In ventilated subjects, the pressures are somewhat different. Due to a muscle relaxation, the subathmospheric pressure created by the diaphragm is often set to 0. From the ventilator, a positive airway pressure is applied to the respiratory system. The endotracheal tube often causes turbulent flow and an additional resistance to air flow ($R_{tube}$) which may be considered by an additional quadratic term $$P_{mund}(1) = \frac{1}{C_{rs}} \cdot (V_{lunge}(t) - V_{lunge,0}) + R_{ström} \cdot \dot{V}_{atem}(t) + R_{tubus} \cdot \dot{V}_{atem}(t) \cdot |\dot{V}_{atem}(t)|. \tag{8}$$

FIG. 6 shows a electrical analog of lung mechanics during pressure controlled ventilation. According to Dalton's law, the partial fractions of all gases in an alveole form the alveolar pressure $$P_{alv}=P_{alv.O_2}+P_{alv.CO_2}+P_{alv.N_2}+P_{alv.H_2O} \tag{9}$$

Note that the steam partial pressure $p_{alv.H_2O}$ is caused by moisturization in the bronchial tree. From eq. (9), it becomes obvious that even at a 100% inspiratory oxygen fraction, $P_{alv.O2}$ will alway be below athmospheric pressure due to the presence of steam and $CO_2$ partial pressure. In fact, considering $P_{alv.H_2O}$=47 mmHg and $p_{alv.CO_2}$=39 mmHg (at 37° C.) results in $$P_{alv.O_2} \leq 674 \text{ mmHg} \tag{10}$$

Thus, during normal pressure ventilation the arterial partial pressure of oxygen may never exceed 674 mm Hg.

From the alveoles to the blood, oxygen is transported by passive diffusion which can be described by Fick's law $$\frac{dV_{O_2}}{dt} = \frac{k \cdot A_{diff}}{l_{diff}} \cdot (p_{alv,O_2} - paO_2) = R_{diff} \cdot (p_{alv,O_2} - paO_2). \tag{11}$$

The gas flow is directly proportional to the area of gas exchange ($A_{diff}$) and in inverse proportion to the diffusion length $l_{diff}$. In healthy subjects, the gas exchange occurs rather fast (<<1 s). Note that the diffusion coefficient for $CO_2$ is approx. 20× larger than the coefficient for $O_2$.

The mechanical large-scale characterics are best described by a pV curve. FIG. 7 give the pV diagrams of a healthy (left) and an ailing (right) lung. Note that the lung volume displayed in these diagrams actually is a relative lung volume (i.e. the actual lung volume minus the absolute lung volume at rest). From these diagrams, the static compliance $C_{rs}$ may be computed at each operating point by $$C_{rs} = \frac{V_T}{PIP - PEEP} \tag{12}$$

Note that a healthy lung has a significant compliance ($C_{rs}$>0) over the whole operating range and may be ventilated with a sufficient tidal volume at typical airway pressures (like e.g. PIP=20 mbar, PEEP=5 mbar).

However, an ailing lung shows a different hysteresis. Especially on the ascending branch, a low tidal volume may occur. In this section of the large-scale characteristic of the lung, a major fraction of alveoles is collapsed and may not participate in gas exchange.

This fact is even more illucidated when watching the large-scale characteristic of $paO_2$. FIG. 8 shows the $paO_2$ of the same healthy (left) and ailing (right) lung. While there is almost no hysteresis in the healthy lung and the choice of ventilation pressures has no visible impact on the quality of gas exchange, the hysteresis is even more severe in an ailing lung. In many cases, $A_{diff}$ may be reduced so strongly that at typical ventilation pressures, a sufficient hemoglobin oxygen saturation (>85 mm Hg) may only be reached if high oxygen concentrations (e.g. 90 . . . 100%) are delivered to the patient.

For such an ailing lung, an optimal ventilation strategy could be to first open the lung with a temporary high airway pressure and then ventilate on the descending branch of the hysteresis such that a sufficient tidal volume is reached and gas exchange is maintained.

The mechanical hysteresis found in healthy lungs (FIG. 7, left) illustrates the fact that there is some alveolar recruitment in healthy lungs as well, but with no visible effect on gas exchange (FIG. 8, left).

For an optimized ventilatory therapy adapted to the individual patient, it is very important to know the static and dynamic properties of his lung. Since the condition of the lung may change significantly within a short period of time, it is important the identify the lung condition as frequent as necessary.

At low air flows, the resistive influence of the endotracheal tube may be linearized and included into $R_{air}$.

Resistance to air flow and respiratory compliance may be computed from the expiratory flow curve. Assuming $R_{air}$ and $C_{rs}$ to be constant during expiration, the following eq. yields $$\hat{R}_{ström} = \frac{PIP - PEEP}{\dot{V}_{atem,max}} \tag{13}$$

and $$\hat{C}_{rs} = \frac{\hat{T}_{rs}}{\hat{R}_{ström}}. \tag{14}$$

As a matter of fact, the expiratory time constant $\hat{T}_{rs}$ may be computed from a least squares fit of the measured expiratory flow curve. Note that both small-scale characteristic parameters change with specific diseases (e.g. $R_{air}$ increases during obstructive diseases), but are also functions of lung volume. Thus, knowing the small-scale characteristics of a specific lung alone may no be sufficient to evaluate the status of a patient. For an optimized ventilation, it is important to know the large-scale status of the lung as well.

For identification of the large-scale characteristics of a lung, a pressure ramp may be used which allows to completely cover the hysteresis. As an example, FIG. 9 shows a pressure ramp which may be used to identify the hysteresis based on arterial oxygen partial pressure.

Note that obtaining the alveolar opening and closing pressures from monitoring $paO_2$ during airway pressure changes is already known from the publication Leonhardt, S., Böhm, S and Lachmann B., "Optimierung der Beatmung beim akuten Lungenversagen durch Identifikation physiologischer Kenngrößen", Automatisierungstechnik (at), Vol. 46, No. 11, pp 532–539, 1998, as mentioned above. With the methods claimed in this invention, the same information may be obtained by using noninvasive measurements instead of the invasive $paO_2$.

To determine alveolar opening and closing pressures, a generally known and accepted definition can be applied. This definition states that a lung is "surely open" if $paO_2$>450 mmHg when the inspiratory oxygen fraction applied to the patient is $fiO_2$=100%. Under the same conditions, a lung is said to be "surely closed" (predominantly collapsed) if $paO_2$<300 mmHg. Note that the $paO_2$ hysteresis as shown in FIG. 8, is completely determined by these alveolar opening and closing pressures.

A known strategy for protective long-term ventilation is to first identify the opening and closing pressures, to afterwards reopen the lung with airway pressures above the opening pressure and then to ventilate with airway pressures shortly above the identified closing pressure.

As shown in FIG. 9, the aim to ventilate requires to use not only a mean airway pressure, but the application of two pressure levels, namely the already mentioned peak inspiratory pressure (PIP) and the positive end-expiratory pressure (PEEP). Thus, during identification of the lung hysteresis an opening and a closing pressure for of each ventilator parameter is obtained. Both values may afterwards be used for automatic ventilation.

In FIG. 10, an application of the method shown in FIG. 9 is shown which in fact offers a protective ventilation strategy. After determination of alveolar opening and closing pressure values for PIP and PEEP, the lung is reopened and afterwards ventilated above alveolar closing pressure. For example, one possibilty to choose PEEP is $$PEEP = PEEP_{close} + 2\ \text{mmHg} \tag{15}$$

and PIP such that the corresponding tidal volume lies within acceptable limits. However, any PIP settings above the corresponding closing pressure are also possible.

Instead of the $paO_2$ signal obtained invasively, the method claimed in this invention utilizes the endtidal $CO_2$ concentration and/or the $CO_2$ output as feedback signals for identification of the optimal ventilator settings for ailing lungs. Both feedback signals can be measured noninvasively. In a preferred implementation of the invention, a closed loop system as given in FIG. 11 is used for automatic ventilation based on endtidal $CO_2$ concentration and/or $CO_2$ output.

The automatic tuning of the ventilator settings may be realized by using an external apparatus (e.g. an additional personal computer) or by integration into the internal ventilator software.

Note that the $CO_2$ output (in [ml $CO_2$/min]) from the body can be obtained from continuous measurements of the $CO_2$ concentration [in %] and air flow (in [ml/min]) and subsequent breathwise computation of $$\dot{V}_{CO_2 Atem} = RR \cdot \int_0^{T_e} [CO_2](t) \cdot \dot{V}_{Atem}(t) DT \tag{16}$$

during expiration. Balancing $CO_2$ production and elimination in the body gives the $CO_2$ content stored in the body $$V_{CO_2 speicher}(t) = V_{CO_2 speicher}(0) + \int_0^t (\dot{V}_{CO_2,prod} - \dot{V}_{CO_2,Atem}) dt. \tag{17}$$

In a paralyzed patient, $CO_2$ production may assumed to be constant, at least within a time frame of some minutes to a few hours. Within this period, additional physiological control mechanisms like the pH control loop via the kidneys can be neglected due to their slow long-term orientation. Typical values for $CO_2$ production are around 5 . . . 7 ml/kg min.

If the $CO_2$ output from the body is reduced due to a partial lung collapse, the like $CO_2$ content stored in the body fluids and also the arterial $paCO_2$='f($V_{CO_2body}$) will increase. FIG. 12 give a schematic diagram to illustrate the computation of $CO_2$ minute volume.

It is known that in healthy lungs with a small fraction of atelectatic alveoles and a small mechanical hysteresis, the $CO_2$ output may be raised by increasing PIP-PEEP (and thus the tidal volume). Of course, in this case $paCO_2$ will drop (remember that $paCO_2$ may also be influenced by changing I/E or RR). In ailing lungs featuring a larger hysteresis, this fact may be employed for identification of the hysteresis characteristics (i.e. alveolar opening and closing pressures).

Before starting an identification procedure based on $CO_2$ output, it is important to obtain a "steady state" at a higher $CO_2$ level. This can be done by choosing a somewhat low RR. If the ventilation pressures are now increased, an alveolar opening can be detected from a sudden increase and possibly an overshoot in $etCO_2$ and $CO_2$ output. As a consequence of the increased $CO_2$ elimination from the body, $V_{CO_2,body}$ and $paCO_2$ will decrease. In contrast to the $paO_2$ signal, both $etCO_2$ and the $CO_2$ output do not stay constant after a successfull alveolar opening, but decrease due to an increased elimination based on a larger gas exchange area.

If the ventilation pressures are afterwards decreased again, an alveolar collapse can be detected from a significant decrease in $etCO_2$ and/or $CO_2$ output.

FIG. 13 shows a pressure ramp which may be used for identification of the large-scale behaviour of an ailing lung based on $etCO_2$ and/or $CO_2$ output. Note that the absolute changes in the $etCO_2$ and/or the $CO_2$ output signal are functions of the initial $paCO_2$. Thus, it is essential to calibrate the identification by an initial blood gas measurement. Furthermore, preferably the initial body $CO_2$ balance is raised (e.g. by reduction of RR) and in steady state.

As an alternative to the method described above, it is also possible to identify alveolar opening and closing by monitoring the relative changes of the $etCO_2$ and/or the $CO_2$ output signal.

After identification of alveolar opening and closing pressures, the lung may be openend again by applying pressures above opening pressure and subsequently be ventilated by setting the PEEP above closing pressure. Since the $etCO_2$ is proportional to $paCO_2$ in an open lung, $paCO_2$ may afterwards be feedback controlled and kept within physiological limits.

Instead of the paO2 signal obtained invasively, in another preferred embodiment of this invention the hemoglobin oxygen saturation ($SO_2$) measured nonivasively is used as a feedback signal for identification of optimal ventilation parameters for ailing lungs.

To apply the method claimed in this invention, it is assumed that the $SO_2$ is valid, i.e. peripheral measurements of hemoglobin oxygen saturation are accessable (the patient is not in shock or centralizing due to other reasons, etc.).

FIG. 14 shows the connection between $paO_2$, physically solved $O_2$ and hemoglobin oxygen saturation. The reference $SO_2$ is set such that $SO_2$ stays within physiological limits (e.g. 80 . . . 100%), but still has a sufficient gradient. A typical value may be $SO_2$=90%.

FIG. 15 shows this preferred embodiment of the invention useful for obtaining a protective automatic ventilation. The automatic setting of ventilation parameters may be realized by meaning of a hemoglobin oxygen saturation sensor and an additional external apparatus or may be integrated into the given hardware of an artificial ventilator.

As has been explained already, in the preferred embodiment of the invention $SO_2$ is not used as a feedback signal directly, but is controlled within a cascaded feedback control loop to stay within given limits. Thus, the inspiratory oxygen fraction ($fiO_2$) required to keep $SO_2$ constant serves as an indirect signal to identify the lung hysteresis By preference, the performance of the $SO_2$ controller is so high that $SO_2$ stays constant even if other ventilation parameters are changed. Under these circumstances, $fiO_2$ serves as an indicator for the fraction of collapsed alveoles. For example, if a high $fiO_2$ is required (e.g. $fiO_2 \geqq 70\%$) to reach $SO_2$=90%, the lung is mainly collapsed. By contrast, if a low $fiO_2$ (e.g. 30%) is sufficient to reach $SO_2$=90%, the lung is mainly open.

This fact may be used to identify the large-scale gas exchange hysteresis of ailing lungs as introduced above. In a preferred embodiment of the invention, the ventilation pressures are modified while $SO_2$ control is active.

FIG. 17 shows pressure ramps which can be used to identify the large-scale gas exchange hysteresis of an ailing lung based on the set $fiO_2$. These curves represent a typical behaviour. However, in a real environment the obtained signals may somewhat differ from these idealized curves. To determine the alveolar opening and closing pressures, the time course of the $fiO_2$ signal required to keep $SO_2$ constant while simultaneously raising the ventilation pressures must be evaluated. For example, a possible feature that could be extracted from the $fiO_2$ time course is the maximal or minimal gradient.

Note that at lower $fiO_2$ levels, the resistance to diffusion is relatively increased. Also, it must be kept in mind that if a lung has been opened and is now ventilated at low pressures and low $fiO_2$ levels, a subsequent collapse is potentially hazardous to the patient. The reason for this danger is that during a collapse, the lung volume decreases very fast. Thus, the now dramatically reduced gas exchange area may not be large enough any more for transfer of sufficient oxygen. In order to avoid an insufficient oxygen supply and possible damage to the patient, the $SO_2$ control is required to react fast.

After successfull identification of the opening and closing pressures and subsequent reopening of the lung, a protective long-term ventilation above the closing pressures as already explained in FIG. 10 is applied.

What is claimed is:

1. Method for determining the alveolar opening or closing of a lung ventilated by an artificial ventilator, comprising the steps of:

measuring the hemoglobin oxygen saturation ($SO_2$), and changing the airway pressure ($P_{aw}$) wherein from the observation of the resulting course of the measured hemoglobin oxygen saturation ($SO_2$) the airway pressure level at which alveolar opening or closing occurs is determined.

2. Method according to claim 1, wherein the inspiratory oxygen fraction ($fiO_2$) at the artificial ventilator is adjusted such that the measured hemoglobin oxygen saturation ($SO_2$) is approximately equal to a given reference value, and wherein the airway pressure is changed and from the resulting course of the adjusted inspiratory oxygen fraction ($fiO_2$) an airway pressure level is determined, which corresponds to the alveolar opening or the alveolar closing of the lung.

3. Method according to claim 2, wherein the airway pressure is increased continuously and wherein an alveolar opening of the lung is detected, if the gradient of the resulting course of the adjusted inspiratory oxygen fraction ($fiO_2$) reaches a negative minimum.

4. Method according to claim 2, wherein the airway pressure is decreased continuously and wherein an alveolar closing of the lung is detected, if the gradient of the resulting course of the adjusted inspiratory oxygen fraction ($fiO_2$) reaches a positive maximum.

5. Method according to claim 3, wherein the airway pressure is decreased continuously and wherein an alveolar closing of the lung is detected, if the gradient of the resulting course of the adjusted inspiratory oxygen fraction ($fiO_2$) reaches a positive maximum.

6. Method for determining the alveolar opening or closing of a lung ventilated by an artificial ventilator, comprising the steps of:

measuring the endtidal $CO_2$ concentration in the expired gas ($etCO_2$), and changing the airway pressure ($p_{aw}$), wherein from the observation of the resulting course of the measured endtidal $CO_2$ concentration the airway pressure level at which alveolar opening or closing occurs is determined.

7. Method according to claim 6, wherein the airway pressure is increased continuously and wherein an alveolar opening of the lung is detected, if the positive gradient of the resulting course of the measured endtidal $CO_2$ concentration and/or the $CO_2$ output reaches a maximal change.

8. Method according to claim 7, wherein the airway pressure is decreased continuously and wherein an alveolar closing of the lung is detected, if the negative gradient of the resulting course of the measured endtidal $CO_2$ concentration and/or the $CO_2$ output reaches a maximal change.

9. Method according to claim 6, wherein the airway pressure is decreased continuously and wherein an alveolar closing of the lung is detected, if the negative gradient of the resulting course of the measured endtidal $CO_2$ concentration and/or the $CO_2$ output reaches a maximal change.

10. Method for determining the alveolar opening or closing of a lung ventilated by an artificial ventilator, comprising the steps of:

measuring the $CO_2$ output ($CO_2$ volume exhaled per unit time), and changing the airway pressure ($p_{aw}$), wherein from the observation of the resulting course of the measured $CO_2$ output the airway pressure level at which alveolar opening or closing occurs is determined.

11. Method according to claim 10, wherein the airway pressure is increased continuously and wherein an alveolar opening of the lung is detected, if the positive gradient of the resulting course of the measured endtidal $CO_2$ concentration and/or the $CO_2$ output reaches a maximal change.

12. Method according to claim 11, wherein the airway pressure is decreased continuously and wherein an alveolar closing of the lung is detected, if the negative gradient of the resulting course of the measured endtidal $CO_2$ concentration and/or the $CO_2$ output reaches a maximal change.

13. Method according to claim 10, wherein the airway pressure is decreased continuously and wherein an alveolar closing of the lung is detected, if the negative gradient of the resulting course of the measured endtidal $CO_2$ concentration and/or the $CO_2$ output reaches a maximal change.

14. Apparatus for determining the alveolar opening or closing of a lung, comprising:

an artificial ventilator for ventilating a lung, a saturation sensor for measuring the hemoglobin oxygen saturation ($SO_2$), and a data processor which determines during a change of the airway pressure ($p_{aw}$) from the resulting course of the measured hemoglobin oxygen saturation ($SO_2$) the airway pressure level at which alveolar opening or closing occurs.

15. Apparatus according to claim 14, comprising a feedback control loop which controls the inspiratory oxygen fraction ($fiO_2$) delivered to the patient such that the measured hemoglobin oxygen saturation ($SO_2$) is approximately equal to a given reference value, and wherein the data processor determines the airway pressure at which alveolar opening occurs from the course of the required inspiratory oxygen fraction ($fiO_2$) during a change of the airway pressure.

16. Apparatus for determining the alveolar opening or closing of a lung, comprising:

an artificial ventilator for ventilating a lung, a sensor to measure endtidal $CO_2$ concentration ($etCO_2$), and a data processor which determines during a change of the airway pressure ($p_{aw}$) from the resulting course of the measured endtidal $CO_2$ concentration the airway pressure level at which alveolar opening or closing occurs.

17. Apparatus for determining the alveolar opening or closing of a lung, comprising:

an artificial ventilator for ventilating a lung, a sensor to measure $CO_2$ output ($CO_2$ volume exhaled per unit time), and a data processor which determines during a change of the airway pressure ($p_{aw}$) from the resulting course of the measured $CO_2$ output the airway pressure level at which alveolar opening or closing occurs.

* * * * *